United States Patent
Depeursinge et al.

(10) Patent No.: US 6,201,476 B1
(45) Date of Patent: Mar. 13, 2001

(54) DEVICE FOR MONITORING THE ACTIVITY OF A PERSON AND/OR DETECTING A FALL, IN PARTICULAR WITH A VIEW TO PROVIDING HELP IN THE EVENT OF AN INCIDENT HAZARDOUS TO LIFE OR LIMB

(75) Inventors: Yves Depeursinge, Servion; Jens Krauss, Neuchatel; Mario El-Khoury, Fontainemelon, all of (CH)

(73) Assignee: CSEM-Centre Suisse d'Electronique et de Microtechnique S.A., Neuchatel (CH)

(*) Notice: Subject to any disclaimer, the term of this patent is extended or adjusted under 35 U.S.C. 154(b) by 0 days.

(21) Appl. No.: 09/434,526

(22) Filed: Nov. 5, 1999

Related U.S. Application Data

(63) Continuation-in-part of application No. 09/073,641, filed on May 6, 1998, now abandoned.

(51) Int. Cl.[7] .................................................. G08B 23/00
(52) U.S. Cl. ................... 340/573.1; 340/573; 340/573.4; 340/529; 340/531; 340/539; 340/579
(58) Field of Search ....................... 340/573, 573.1, 340/573.4, 529, 539, 531, 579, 589, 693

(56) References Cited

U.S. PATENT DOCUMENTS

| | | | | |
|---|---|---|---|---|
| 5,045,839 | * | 9/1991 | Ellis et al. ........................ | 340/539 |
| 5,652,570 | * | 7/1997 | Lepkofker ...................... | 128/662.03 |
| 5,670,944 | * | 9/1997 | Myllymaki ...................... | 340/573 |
| 5,853,005 | * | 12/1998 | Scanlon ........................ | 128/662.03 |
| 5,940,004 | * | 8/1999 | Fulton ........................... | 340/825.49 |

* cited by examiner

*Primary Examiner*—Daniel J. Wu
*Assistant Examiner*—Hung Nguyen

(57) ABSTRACT

A device for monitoring the activity of a person and/or detecting a fall suffered by a person with a view in particular to summoning help in the event of an incident hazardous to life or limb is worn by the person concerned and transmits a danger signal to a remote monitoring center. The device generates acceleration, speed and/or position signals representative of the behavior and/or the spatial attitude of the person. It establishes a probability factor representative of the probability that a dangerous situation is present from how the acceleration, speed and position signals change with time. It triggers in accordance with the value of the probability factor an alarm generator capable of causing the danger signal to be transmitted to the center.

9 Claims, 2 Drawing Sheets

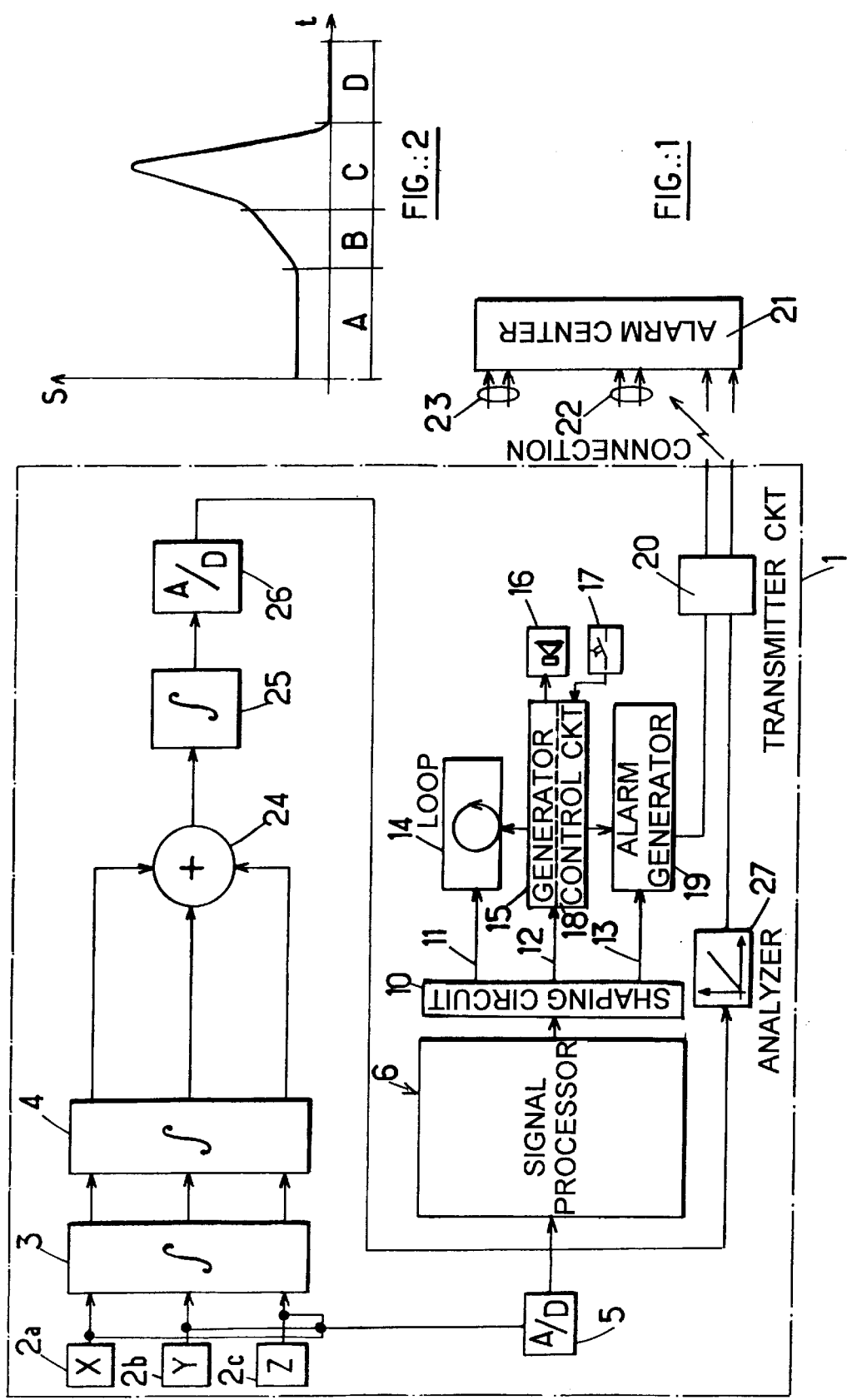

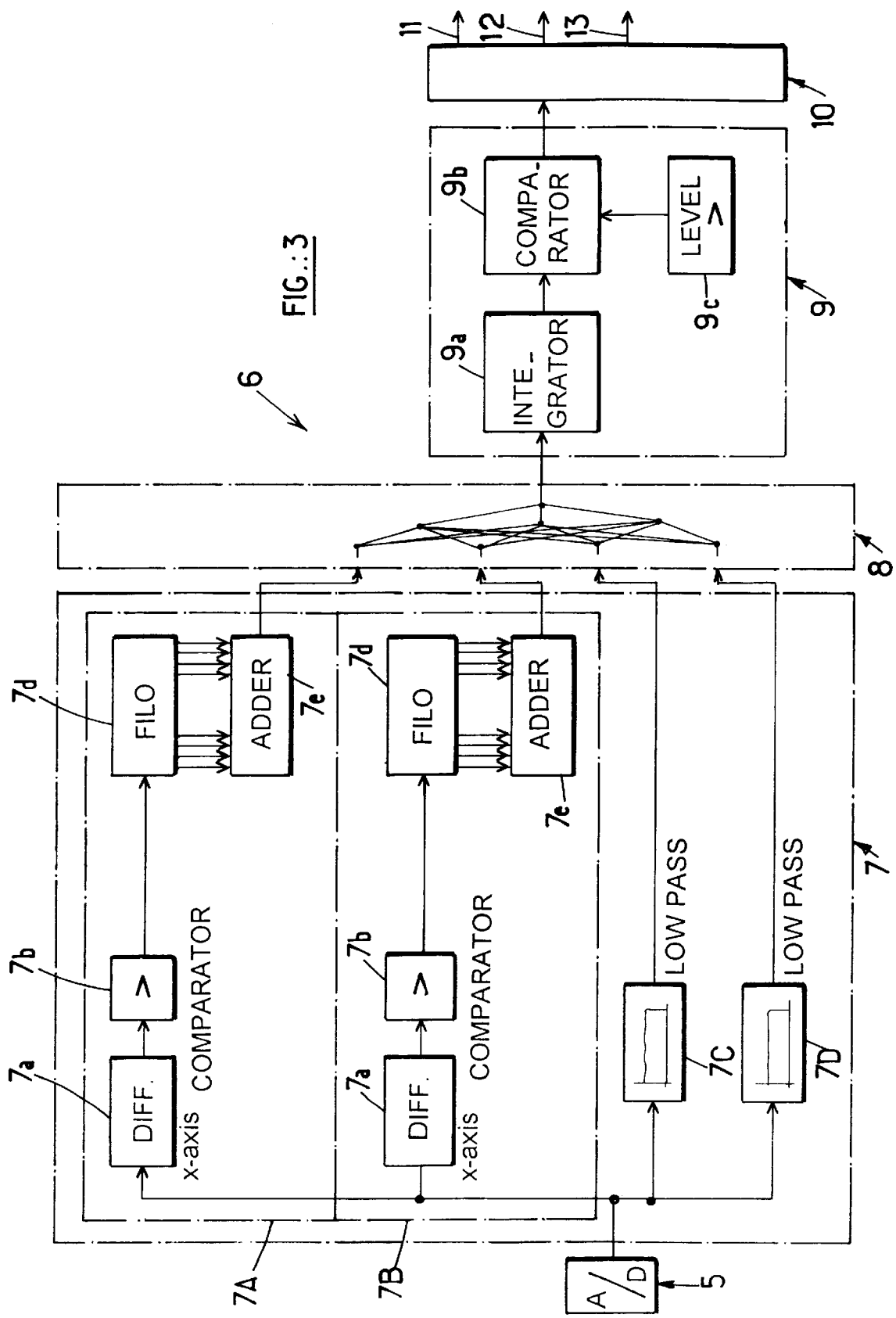
FIG.:3

US 6,201,476 B1

DEVICE FOR MONITORING THE ACTIVITY OF A PERSON AND/OR DETECTING A FALL, IN PARTICULAR WITH A VIEW TO PROVIDING HELP IN THE EVENT OF AN INCIDENT HAZARDOUS TO LIFE OR LIMB

This Application is a Continuation in part (cip) of 09/073,641, filed on May 6, 1998 now abandoned.

BACKGROUND OF THE INVENTION

1. Field of the Invention

The present invention concerns a device for monitoring the activity of a person and/or detecting a fall, in particular with a view to providing help in the event of an incident hazardous to life or limb. An incident of the above kind can be a fall suffered by the person, for example.

2. Description of the Prior Art

There currently exist networks for monitoring persons, in particular elderly persons, comprising a monitoring center able to call in helpers (qualified medical personnel, neighbors, family members, etc) in response to alarms that can be generated by the persons monitored. The latter are usually in their home which is within the coverage area of the network and can therefore, in the event of an incident, alert the monitoring center by operating an alarm button on a unit worn on the wrist or around the neck, for example. The unit contains an alarm signal generator providing a wireless connection to a home unit that transmits the signal to the monitoring center, usually via the public switched telephone network.

A problem with this type of alert procedure is that it requires the intervention of the person at risk (active alarm implying action by the wearer) with the result that if the situation is serious to the point of causing panic in the person affected, total immobilization or even total loss of consciousness, no alarm signal can be sent Furthermore, existing systems do not include any means of determining if the unit is actually being worn by the person.

An aim of the invention is to propose a device of the general type indicated hereinabove which remedies the drawbacks of prior art monitoring devices.

SUMMARY OF THE INVENTION

The invention therefore consists in a device for monitoring the activity of a person and/or detecting a fall suffered by a person with a view in particular to summoning help in the event of an incident hazardous to life or limb, the device being adapted to be worn by the person and including means for transmitting a danger signal to a remote monitoring center, the device further including:

means for generating acceleration, speed and/or position signals representative of the behavior and/or the spatial attitude of the person, means for establishing a probability factor representative of the probability that a risk is present from how the acceleration, speed and position signals change with time; and means for triggering in accordance with the value of the probability factor an alarm generator capable of causing the danger signal to be transmitted to the center.

The monitoring device preferably further includes means for monitoring the activity of the person.

As a result of the above features, although intentional action remains possible, the monitored person does not need to be involved in the procedure of alerting the monitoring center, which constitutes an evident safety improvement.

The features stated hereinabove enable other advantageous features to be provided for facilitating analysis of the risk situation by the monitoring personnel. The invention thus makes it possible to examine sudden changes in the behavior of a monitored person and therefore to deduce very quickly from the signals transmitted to the monitoring center which personnel, what type of help, which equipment, etc is needed to provide affective assistance to the person at risk.

Other features and advantages of the invention will become apparent from the following description given by way of example only and with reference to the accompanying drawings.

BRIEF DESCRIPTION OF THE DRAWINGS

FIG. 1 is a block diagram of a monitoring device in accordance with the invention.

FIG. 2 is a graph showing as a function of time one example of a composite acceleration, speed and/or position signal such as may be generated in the event of a monitored person suffering a fall;

FIG. 3 is a detailed circuit diagram of some components of the monitoring device according to the invention.

DETAIL DESCRIPTION OF THE PREFERRED EMBODIMENT

FIG. 1 is a simplified block diagram of a device constituting one preferred embodiment of the invention for monitoring the behavior of a person. The monitoring device inside the rectangle 1 in FIG. 1 can be accommodated in a unit that the person can wear, for example on the thorax, on a belt or using any other appropriate attachment means.

The monitoring device 1 comprises three accelerometers 2a, 2b and 2c adapted to measure the acceleration of the unit in three orthogonal directions X, Y and Z, the direction Z being the vertical direction when the wearer is standing. The respective acceleration signals $\alpha_x$, $\alpha_y$ and $\alpha_z$ delivered by the accelerometers 2a through 2c are fed to two successive integrators 3 and 4 which respectively supply the speeds $v_x$, $v_y$ and $v_z$ of the thorax of the wearer and its spatial position $p_x$, $p_y$, $p_z$. The signals generated at the output of accelerometers 2a through 2c are fed to an analog/digital (A/D) converter 5. The signals from the A/D converter 5 are fed to a signal processor circuit 6 including three processor units 7, 8 and 9 of which a more detailed circuit diagram is given in FIG. 3.

In the embodiment described, it is supposed that only two acceleration signals are considered among the three digital acceleration signals supplied by converter 5. It is considered that this may be sufficient to obtain an adequate behavior analysis. Of course, the monitoring device can also be designed so as to handle three acceleration signals. In the example described, the accelerations according to the x-axis and the z-axis are analyzed i.e. the acceleration in the horizontal and the vertical directions.

Unit 7 thus comprises for each of the x and z axes a computation circuit, 7A and 7B, respectively wherein, in order to afford information about the dynamic behavior of the person, the acceleration signal of the relevant axis is computed as follows.

Each computation circuit 7A and 7B comprises a block 7a which performs the computation of a difference $\Delta\alpha = \alpha(tk) - \alpha(tk-1)$, wherein $\alpha$ is the relevant acceleration value for the corresponding axis and tk the time at which the acceleration sample is taken. The sampling rate is fixed at a given time interval which may be equal to 40 milliseconds, for example. Thus, $\Delta\alpha$ represents the variation of the acceleration between two successive samples for the corresponding x or z axis.

Block 7a is connected to a comparator 7b wherein the difference signal $\Delta\alpha$ is compared to a predetermined level. If the signal $\Delta\alpha$ exceeds the level, it is transferred to the output of comparator 7b. If not, the output signal of comparator 7b equals zero.

Comparator 7b is connected to a FILO register (First In Last Out) wherein successive values output by adder 7c are shifted at the sampling rate. The cells of FILO 7d are connected to an adder 7e which sums up the contents thereof also at the sampling rate. For example, if samples are taken at a time interval of 40 milliseconds, and the FILO comprises 50 cells, then the output of adder 7e generates a global entropy value taken over two seconds representing the sum of 50 instantaneous entropy values, whereby successive global values are produced at the sampling rate.

It must be understood that the foregoing description of the computation circuits 7A and 7B is given by way of example only. Its implementation may be made in a different manner or the functions of the computation circuits may be carried out by software without departing from the scope of the invention.

Unit 7 also comprises, for each of the respective x and z axes, a low pass filter, 7C and 7D respectively, filtering each of the acceleration signals supplied by converter 5 for detection therein the DC component of the signal. This component represents the variations of the wearer's posture.

Unit 8 carries out a behavior analysis using an artificial neural network that continuously monitors the signals output by unit 7. Neural networks that can be used for this purpose are described in an article by A. Jain, J. Mao and K. Mohuiddin published in the March 1996 issue of the IEEE review. Such a neural network comprises a plurality of nodes distributed among a given number of layers, the nodes of each layer being connected to all the nodes of the adjacent layers. The nodes of the first and the last layer are connected to the inputs and the outputs, respectively. Data are transmitted through the network along the connections between the nodes. Each transmission is carried out by applying to the data given weighting and bias coefficients. Usually, the computation is made by software.

The weighting and bias coefficients of this network are determined by a learning process. The learning process is carried out with actual data trials whereby a mapping is obtained comprising weighting and bias coefficients. Such coefficients are so computed that for given values of input signals supplied by unit 7 and obtained during the trials, a probability rate is generated as an output signal of the network, such output signal being represented by a value which can be in the range of 0 to 1, the value 0 representing a certainty of fall and the value 1 a certainty of no fall. Preferably, determining of weighing and biasing coefficients is done once and for all. This can be done using the Marquardt algorithin, as described in a paper from Martin T. Hagan and Mohamed B. Menhaj, entitled "Training Feedforward Networks with the Marquardt Algorithm" and presented to the IEEE Conference on Neural Networks, June 1994.

Unit 9 is connected to the output of neural network 8. It comprises an integrator 9a, a comparator 9b connected to the output of the integrator 9a and a level generator 9c connected to the comparator 9b. Integrator 9a integrates periodically the output signal of neural network 8 during a given time period (a few milliseconds for example). The result of the integration is applied to comparator 9b in order to be compared with several levels. There may be three levels for example representing respectively a high, a medium and a low probability of fall. The output of comparator 9b is applied to shaping circuit 10 comprising outputs 11, 12 and 13 on which may appear selectively a high, medium or low probability of fall signal.

In order to save power consumption of the monitoring device, it may be contemplated to put units 8 and 9 in a standby mode of operation, if no dynamic changes in the acceleration signals are detected.

FIG. 2 shows a typical diagram as a function of time of the signal prior to digitization in the converter 5 and then subjected to an analysis leading to an alarm situation. The person behaves normally during a first phase A in which the indicator signal is substantially constant During phase B the wearer starts to fall and during phase C this leads to an impact due to the fall. In phase D the meaningful signal is at zero, the wearer being immobile and probably unconscious or at least incapable of reacting or getting up.

As long as a low probability signal is present at output 11 a wait loop 14 is active, pending a change in the probability factor. If a medium probability factor subsequently appears at the output 12, a generator 15 sends a warning signal to a loudspeaker 16 incorporated into the unit housing the monitoring device 1. The sound produced by the loudspeaker 16 invites the wearer to indicate that they are conscious. Despite the medium probability of danger level, the wearer operates a button 17 on the unit housing the monitoring device 1 if they are capable of doing this. The signal generated in this way is processed in a control circuit 18 which transmits a command signal to the wait loop 14 to reactivate it.

If the button 17 is not operated, on the other hand, the control circuit sends a signal to an alarm generator 19. The latter is connected to a transmitter circuit 20 which can format the alarm signal for transmission by any appropriate means to an alarm center 21 or trigger a call to rescue personnel. This center can receive similar information from other monitoring devices in the network served by the center 21, as symbolized by the connections 22 and 23 in FIG. 1.

The signals from the integrator 4 are advantageously fed to a summing device 24 producing a signal analyzing the activity of the wearer which is fed to an integrator 25 integrating it over a predetermined time period, for example one minute. After conversion in an analog/digital converter 26 the signal is fed to an activity analyzer unit 27 which, on the basis of predefined criteria, sends an activity signal to the center 21 via the transmitter circuit 20.

It is generally possible either to transmit the activity data to the external center for remote processing or to process the data locally using appropriate circuits. Other applications are then feasible, for example diet control, monitoring of rest times, etc.

Of course, the wearer can also trigger the alarm intentionally in the alarm generator 19 by means of a control circuit 18, by pressing the button 17 at their own initiative.

Analysis of the acceleration signals supplied by the accelerometers 2a, 2b and 2c provides an additional and beneficial function in that it is possible to determine if the monitoring device is being worn or not If not, an alarm can be generated and transmitted to the center 21 after a predetermined time-delay from registering the fact that the device has been taken off.

Likewise, it can detect if the person has lost consciousness or has even ceased breathing.

The monitoring device of the invention can be made from discrete or modular circuits and/or components but is preferably implemented in the form of an appropriately programmed microprocessor.

What is claimed is:

1. A device for monitoring the activity of a person and/or detecting a fall suffered by a person with a view in particular to summoning help in the event of an incident hazardous to life or limb, said device being adapted to be worn by said person and including means for transmitting a danger signal to a remote monitoring center, said device further including:

means for generating multiple acceleration signals representative of the behavior and/or the spatial attitude of said person;

means for establishing a probability factor representative of the probability that a risk situation is present from how said multiple acceleration signals change with time; and means for triggering in accordance with the value of said probability factor an alarm generator capable of causing said danger signal to be transmitted to said center.

2. The monitoring device claimed in claim 1 wherein said means for generating multiple acceleration signals include at least two accelerometers adapted to detect acceleration of at least a portion of the body of said person and integrator means for two-fold integration of signals delivered by said accelerometers.

3. The monitoring device claimed in claim 1 wherein said means for establishing said probability factor include an artificial neural network the bias and weighting values of which are determined by a learning process.

4. The device claimed in claim 1 wherein said means for establishing said probability factor further include means for evaluating the behavior of said person before and after said incident.

5. The monitoring device claimed in claim 1 wherein said means for producing said probability factor include means for evaluating the dynamic behavior of said person.

6. The monitoring device claimed in claim 1 wherein said means for triggering an alarm generator include a wait loop adapted to remain activated for as long as the value of said probability factor continues to be representative of a situation such that said person is not at risk.

7. The device claimed in claim 1 wherein said means for triggering said alarm generator include signaling means for indicating to said person a predetermined level of said probability factor and means for manually preventing triggering of said alarm generator if said person is aware of said level.

8. The device claimed in claim 7 wherein said signaling means comprise a loudspeaker incorporated in a unit housing said device and said means for preventing triggering of said alarm generator are formed by a control button on said unit.

9. A device as claimed in claim 1 further including means for analyzing the activity of said person and for transmitting the result of said analysis to said center.

* * * * *